(12) United States Patent  (10) Patent No.: US 7,749,771 B2
Burgess-Cassler et al.  (45) Date of Patent: Jul. 6, 2010

(54) DEVICE AND METHODS FOR DETECTING AN ANALYTE IN A SAMPLE

(75) Inventors: Anthony Burgess-Cassler, Vancouver, WA (US); Lawrence A. Salvo, Miami Beach, FL (US); Luis Alejandro Agudelo, Sunny Isles Beach, FL (US)

(73) Assignee: Rapid Medical Diagnostics Corporation, North Bay Village, FL (US)

( * ) Notice: Subject to any disclaimer, the term of this patent is extended or adjusted under 35 U.S.C. 154(b) by 658 days.

(21) Appl. No.: 11/400,512

(22) Filed: Apr. 7, 2006

(65) Prior Publication Data

US 2007/0054414 A1  Mar. 8, 2007

Related U.S. Application Data

(60) Provisional application No. 60/669,482, filed on Apr. 7, 2005.

(51) Int. Cl.
*G01N 33/53* (2006.01)
(52) U.S. Cl. .................. 436/514; 436/518; 436/164; 436/169; 436/805; 436/807; 436/808; 436/809; 436/810; 435/7.1; 435/7.9; 435/287.1; 435/287.7; 435/970; 422/56; 422/57; 422/58; 422/60; 422/61
(58) Field of Classification Search ................. 436/514, 436/518, 164, 169, 807, 808, 809, 805, 810; 435/7.9, 287.1, 287.7, 287.8, 970; 422/56, 422/57, 58, 60, 61
See application file for complete search history.

(56) References Cited

U.S. PATENT DOCUMENTS

| 4,943,522 | A |   | 7/1990  | Eisinger et al. |
| 5,137,808 | A |   | 8/1992  | Ullman et al. |
| 5,714,341 | A | * | 2/1998  | Thieme et al. ................. 435/22 |
| 5,935,864 | A |   | 8/1999  | Schramm et al. |
| 6,214,291 | B1 |  | 4/2001  | Kerman |
| 6,248,598 | B1 |  | 6/2001  | Bogema |
| 6,303,081 | B1 |  | 10/2001 | Mink et al. |
| 6,634,243 | B1 |  | 10/2003 | Wickstead et al. |
| 6,863,866 | B2 |  | 3/2005  | Kelly et al. |
| 6,875,185 | B2 | * | 4/2005  | Wong et al. .................. 600/584 |
| 7,225,689 | B2 |  | 6/2007  | Wickstead et al. |

FOREIGN PATENT DOCUMENTS

WO  WO 88/08534  11/1988

* cited by examiner

*Primary Examiner*—Bao-Thuy L Nguyen
(74) *Attorney, Agent, or Firm*—Townsend and Townsend and Crew LLP (57) ABSTRACT

Disclosed is a device, for detecting an analyte in a sample, comprising a sample pad for collecting the sample, a test strip coupled to the sample pad, and a housing enclosing and allowing visualization of the test strip. The sample pad can include one or more markings for determining the amount of sample collected. The device can also include a run fluid container that fits over the sample pad and forms an air-tight seal around the housing. Further, the device can include a second sample pad/test strip combination for detection of a second analyte. Also disclosed are methods for detecting an analyte in a sample using the device.

12 Claims, 8 Drawing Sheets

DEVICE AND METHODS FOR DETECTING AN ANALYTE IN A SAMPLE

CROSS-REFERENCES TO RELATED APPLICATIONS

This application claims benefit of U.S. Patent Application No. 60/669,482, filed Apr. 7, 2005, the disclosure of which is incorporated herein in its entirety.

BACKGROUND OF THE INVENTION

The present invention relates generally to devices and methods for detecting an analyte in a sample. More specifically, the present invention provides devices and methods for rapidly testing a sample for an analyte. Generally, "rapid testing" devices are sample testing devices that rely on the development of a visual and typically non-quantitative signal on the surface of a substrate, such as a membrane. Among rapid tests first used were simple pregnancy tests.

The basic "lateral flow test strip" design is typical now of many tests, including veterinary tests, environmental tests, and clinical diagnostics (disease state) tests. One feature of such tests is that they often can be stored under ambient conditions, and they may not require extensive training in order to run and read them. Such features have made them quite useful for assisting in the diagnoses of diseases like HIV, which affects millions of persons in the developing countries of the world. Rapid testing devices are disclosed in, for example, U.S. Pat. Nos. 5,935,864 and 6,303,081.

Countries lacking an extensive medical infrastructure generally do not have the personnel or the facilities and equipment necessary to collect and process large numbers of clinical samples in a centralized laboratory. Hence, a disproportionate number of individuals (compared to nations with more elaborate medical infrastructures in place) may harbor infections and not know how they are infected. Simplicity, ease of sample collection and use, and protection of the user from exposure to biological fluids are high priorities when developing such a device.

A number of problems arise when clinical diagnostics are being developed. Besides stability issues relating to a product's shelf life (these can be overcome by incorporating appropriate dry chemistries, desiccation of the test, and packaging materials that allow only very low levels of moisture transmission) and especially when diagnostics are being developed for use in places like developing countries, means need to be found that (a) maintain a low overall cost for parts and manufacturing, (b) protect and maintain the integrity of the test strip itself, and (c) combine sample collection within the platform itself, in order to make a test as easy and foolproof as possible to use.

BRIEF SUMMARY OF THE INVENTION

The present invention provides devices and methods for rapid testing and analysis of a sample for the presence or absence of an analyte.

Some embodiments of the present invention may be configured to collect and test different bodily fluids from human or animal subjects (e.g., samples comprising oral fluid, blood-based fluids (including whole, undiluted blood), other bodily fluids such as, for example, spinal fluid or urine), as well as samples for chemical or environmental evaluations, with or without diluent or reagent. In particular, the present invention may provide an inexpensive, single-use lateral flow device that will, for example, aid a user (e.g., a physician or other health care provider) in the diagnosis of an infectious disease.

Further, some embodiments of the present invention provide a sample testing device that protects the test strip from contamination as well as protects the user from test samples containing infectious or toxic agents.

Other variations of the present invention provide a sample testing device that allows for visual monitoring of sample volume or amount by the user.

Still further, certain embodiments of the present invention provide ease of manufacture, low cost, and simplicity of use for a sample testing device. In particular, the present invention may provide such a device having flexibility in its use with lateral flow test strips, due to the ease with which the housing length is adjusted, as well as allowing for use of different absorbent collection tip shapes and sizes for specific sample quantities.

Accordingly, in one embodiment, the device for performing a test reaction on a sample to detect an analyte includes a sample pad for collecting the sample; a test strip coupled to the sample pad, the test strip including an indicator region configured to provide a visual indication of the presence or absence of the analyte in the sample; a housing that includes a first end and a second end, wherein the test strip is disposed within the housing, the housing allowing visualization of the test strip, and wherein at least a portion of the sample pad extends beyond the first end of the housing; and a run fluid container configured to be positioned over the portion of the sample pad that extends beyond the first end of the housing, the run fluid container configured to form an air-tight seal around the first end of the housing. The run fluid container can contain a suitable diluent for running the test reaction. Further, in some embodiments, the device includes a flexible collar at the first end of the housing, wherein the flexible collar allows insertion of the sample pad and the test strip into the housing and is configured to maintain coupling of the test strip to the sample pad. The flexible collar, run fluid container, and/or test strip can comprise a color providing a visual indication of the test reaction to be performed. Some variations of the device also include at least one marking on the sample pad providing a visual indication of the amount of sample collected. The device can be configured for collection and testing of a fluid sample or a dry sample.

In some embodiments, the device as set forth above is a dual test strip device. In these embodiments, the sample testing device above further includes a second sample pad for collecting a second sample; and a second test strip coupled to the second sample pad, the second test strip including a second indicator region configured to provide a visual indication of the presence or absence of a second analyte in the second sample; wherein the second test strip is disposed within the housing, the housing allowing visualization of the second test strip, and wherein at least a portion of the second sample pad extends beyond the second end of the housing. The dual test strip device can also include a second run fluid container configured to be positioned over the portion of the second sample pad that extends beyond the second end of the housing, the second run fluid container configured to form an air-tight seal around the second end of the housing. Typically, the dual test strip device further includes a fluid-impermeable element that separates the first and second sample pad.

In another embodiment, the device for performing a test reaction on a sample to detect an analyte includes a sample pad for collecting the sample, the sample pad including at least one marking providing a visual indication of the amount of sample collected; a test strip coupled to the sample pad, the test strip including an indicator region configured to provide a visual indication of the presence or absence of the analyte in the sample; and a housing including a first end and a second end, wherein the test strip is disposed within the housing, the housing allowing visualization of the test strip, and wherein at least a portion of the sample pad extends beyond the first end of the housing. In some variations, the sample pad includes at least two markings providing a visual indication of the amount of sample collected. Particularly suitable are a first marking indicating a minimum amount of sample sufficient for performing the test reaction, and a second marking indicating a maximum amount of sample for performing the test reaction. The device can further include a run fluid container configured to be positioned over the portion of the sample pad that extends beyond the first end of the housing. The run fluid container can contain a suitable diluent for running the test reaction. Further, in some embodiments, the device includes a flexible collar at the first end of the housing, wherein the flexible collar allows insertion of the sample pad and the test strip into the housing and is configured to maintain coupling of the test strip to the sample pad. The flexible collar, run fluid container, and/or test strip can comprise a color providing a visual indication of the test reaction to be performed. The device can be configured for collection and testing of a fluid sample or a dry sample.

In some embodiments, the device as set forth above is a dual test strip device. In these embodiments, the sample testing device further includes a second sample pad for collecting a second sample; and a second test strip coupled to the second sample pad, the second test strip including a second indicator region configured to provide a visual indication of a second test reaction with the second sample; wherein the second test strip is disposed within the housing, the housing allowing visualization of the second test strip, and wherein at least a portion of the second sample pad extends beyond the second end of the housing. The dual test strip device can also include a second run fluid container configured to be positioned over the portion of the second sample pad that extends beyond the second end of the housing. Typically, the dual test strip device further includes a fluid-impermeable element that separates the first and second sample pad.

In another embodiment, the present invention provides a dual test strip device for performing first and second test reactions to detect, respectively, first and second analytes in first and second samples, the dual test strip device including a first sample pad for collecting the first sample; a first test strip coupled to the first sample pad, the first test strip including a first indicator region configured to provide a visual indication of the presence or absence of the first analyte in the first sample; a second sample pad for collecting the second sample; a second test strip coupled to the second sample pad, the second test strip including a second indicator region configured to provide a visual indication of the presence or absence of the second analyte in the second sample; and a housing comprising a first end and a second end, wherein the first and second test strips are disposed within the housing, the housing allowing visualization of the first and second test strips, and wherein at least a portion of the first sample pad extends beyond the first end of the housing and at least a portion of the second sample pad extends beyond the second end of the housing. Typically, the dual test strip device further includes a fluid-impermeable element that separates the first and second sample pad. A particularly suitable configuration for the first and second test strips in the housing is a back-to-back configuration. In some variations, the first analyte to be detected is different in type from the second analyte. Further, in certain embodiments, the samples corresponding to the first and second test reactions to be performed are different in type. One or both of the sample pad/test strip combinations can be configured for collection and testing of a fluid sample. In certain variations, one or both of the sample pad/test strip combinations can also be configured for collection and testing of a dry sample.

In some embodiments, the device as set forth above further includes a first run fluid container configured to be positioned over the portion of the first sample pad that extends beyond the first end of the housing; and, optionally, a second run fluid container configured to be positioned over the portion of the second sample pad that extends beyond the second end of the housing. At least one of the first and second run fluid containers can contain a diluent. At least one of the first and second ends of the housing can also include a flexible collar that allows insertion of the respective sample pad and corresponding test strip into the housing and is configured to maintain coupling of the test strip to the sample pad. At least one of the flexible collar(s), run fluid container(s), and test strip(s) can comprise a color providing a visual indication of the test reaction to be performed. For example, in some variations, both the first and second test strips comprise a color corresponding to the test reactions to be performed. Further, one or both of the sample pads can include at least one marking providing a visual indication of the amount of sample collected. For example, in some embodiments, the sample pad includes at least two markings providing a visual indication of the amount of sample collected. Particularly suitable are a first marking indicating a minimum amount of sample sufficient for performing the test reaction, and a second marking indicating a maximum amount of sample for performing the test reaction.

In another aspect, the present invention provides a method for detecting an analyte in a sample. In one embodiment, the method includes the following steps: contacting a substance to be tested with a sample pad, wherein the sample pad is coupled to a test strip having an indicator region configured to provide a visual indication of the presence or absence of the analyte; retaining contact of the substance with the sample pad until a sample of the substance is collected; positioning a run fluid container over the sample pad so that the run fluid container forms an air-tight seal around a first end of a housing that contains the test strip; allowing the sample to progress through the sample pad and onto the test strip; and reading the presence or absence of the analyte from the indicator region on the test strip.

In another embodiment, the method for detecting an analyte in a sample includes the following steps: contacting a substance to be tested with a sample pad, wherein the sample pad is coupled to a test strip having an indicator region configured to provide a visual indication of the presence or absence of the analyte; retaining contact of the substance with the sample pad until a sample of the substance is collected; determining whether the amount of the sample collected is sufficient for performing the test reaction or exceeds a maximum amount for performing the test reaction; allowing the sample to progress through the sample pad and onto the test strip; and reading the presence or absence of the analyte from the indicator region on the test strip. In certain variations, determining the amount of sample collected is at least partially based on at least one marking on the sample pad, the marking providing a visual indication of the amount of sample collected.

In yet another embodiment, the method is a method using a dual test strip device for performing first and second test reactions to detect first and second analytes in first and second samples, the method including the following steps: contacting a first substance to be tested with a first sample pad, wherein the first sample pad is coupled to a first test strip having a first indicator region configured to provide a visual indication of the presence or absence of the first analyte; retaining contact of the first substance with the first sample pad until a first sample is collected; contacting a second substance to be tested with a second sample pad, wherein the second sample pad is coupled to a second test strip having a second indicator region configured to provide a visual indication of the presence or absence of the second analyte, and wherein the second test strip is coupled to the first test strip in a back-to-back configuration; retaining contact of the second substance with the second sample pad until a second sample is collected; allowing the first sample to progress through the first sample pad and onto the first test strip; allowing the second sample to progress through the second sample pad and onto the second test strip; reading the presence or absence of the first analyte from the first indicator region on the first test strip; and reading the presence or absence of the second analyte from the second indicator region on the second test strip.

In certain embodiments of the method for detecting an analyte, the substance to be tested (or, if performing the dual test strip method, at least one of the first and second substances to be tested) is a fluid such as, for example, a biological fluid (e.g., an oral fluid, blood, spinal fluid, or urine). In other embodiments, the substance to be tested (or, if performing the dual test strip method, at least one of the first and second substances to be tested) is for a chemical or environmental evaluation of the substance.

BRIEF DESCRIPTION OF THE DRAWINGS

FIGS. 3A-3C show collection of a fluid sample with a sample pad having a die-cut-out to regulate the uptake of fluid.

FIGS. 4A-4D show an exemplary embodiment of assembly of a sample testing device of the present invention.

FIGS. 7A-7C show an example of use of a sample pad with a run fluid container containing a diluent.

DETAILED DESCRIPTION OF THE INVENTION

In one aspect, the present invention provides a device for testing a sample of a substance to be tested. The device of the present invention addresses (a) attaching the sample collection portion of the device to the test strip (e.g., the base of the test strip); (b) encasing the test strip within a housing (this protects the portion of the strip that provides the stage for the visible result, namely the membrane), with the sample collection portion at least partially protruding from the end of the housing; (c) providing an housing that allows visualization of the test strip (e.g., an essentially clear housing), so the test result can easily and readily be seen through it; (d) providing an appropriate sample collection material (e.g., for human biological fluids (including, but not limited to, oral fluids and blood or blood components)); (e) providing a means whereby the amount of sample collected may be monitored in a semi-quantitative fashion (typically visually); (f) providing a suitable container that matches the sample collection end of the device, in terms of dimensional fit of the collector to the interior of the container, and its ability when used with the device, to isolate the sample from the user; and (g) closing the housing at the distal end (yet typically leaving a small hole to equalize air pressure) in order to further isolate the test strip from the environment and to further help prevent exposure to the sample, thereby preventing exposure to potentially hazardous substances such as, for example, biological samples containing an infectious agent.

Figure 1:
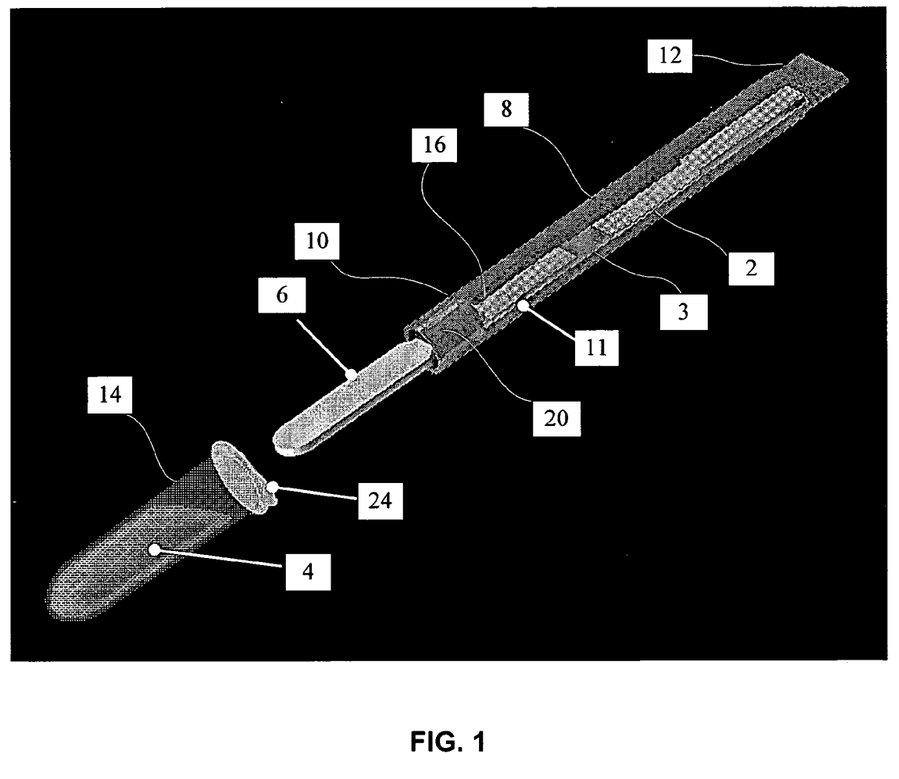
FIG. 1 shows one embodiment of the sample testing device of the present invention comprising a single sample pad/test strip combination.

Referring to FIG. 1, in one embodiment of the device, the device comprises a test strip 2 and, optionally, a corresponding run fluid (diluent) 4; sample pad 6; a housing 8 having ends 10 and 12; and, optionally, a run fluid container 14. The test strip 4 comprises an indicator region 3. Typically, the test strip 2 is a lateral flow test strip such as those known in the art for use in rapid testing of fluid samples. Test strip 2 is disposed within housing 8 and is coupled to sample pad 6 at base 16 of test strip 2, forming an overlap region 7 between test strip 2 and sample pad 6. The base 16 of test strip 2 is positioned at or near the end 10 of housing 8. A portion 18 of sample pad 6 extends beyond the end 10 of housing 8. In certain embodiments, test strip 2 is "tacked" to sample pad 6, such as, for example, with an adhesive. Sample collection assembly 11 comprises test strip 2, sample pad 6, and housing 8 (and optionally cover 32 (not shown in FIG. 1) and/or flexible collar 20, described further herein).

Housing 8 is of sufficient rigidity to maintain device integrity. Housing 8 includes at least a region having sufficient clarity to allow visual inspection and interpretation of enclosed test strip 2. For example, housing 8 may be made of a clear material (such as, e.g., polyethylene or mylar) or may include a visually clear window or cutout that allows for visual inspection of test strip 2. End 12 (distal to the end 10 at which the sample 6 is positioned) is typically sealed (e.g., crimp-sealed). In certain variations, housing 8 includes one or more icons or lettering on its surface, and/or coloring or labeling, providing an indication to the user of any of various parameters for use of the device, including, for example, the type of test reaction corresponding to test strip 2. The distal orientation of end 12 with respect to the sample pad 6 extending from end 10 of the housing facilitates easy handling of sample collection assembly 11.

In certain embodiments, housing 8 is a made of a material that can easily be cut. This feature facilitates adaptability of the device, allowing, e.g., accommodation of test strips of different lengths. For example, in one preferred embodiment, housing 8 is made of blown plastic tubing (e.g., blow molded polyethylene).

Figure 2:
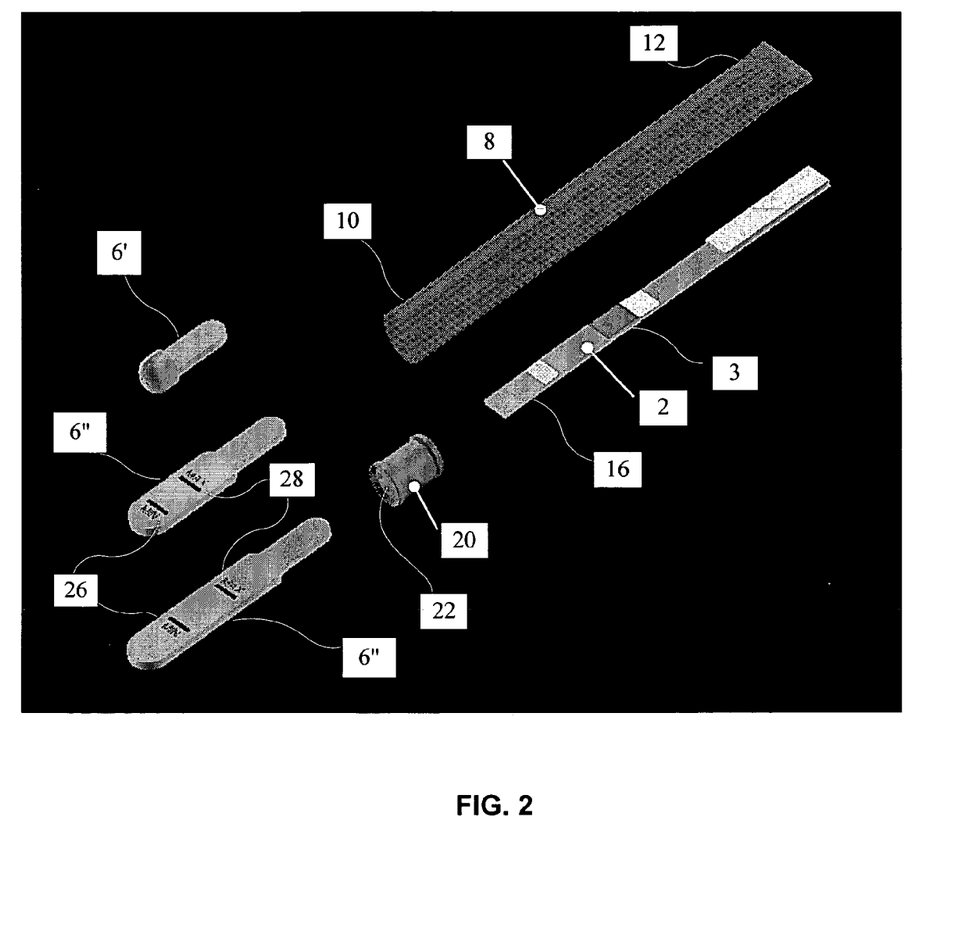
FIG. 2 shows separate components of an embodiment of the sample testing device comprising a single sample pad/test strip combination.

Sample pad 6 can be any member configured to collect a dry or fluid sample and that will facilitate progression of the sample distally from the point of uptake to the test strip 2. In the case of a fluid sample, sample pad 6 can be configured to collect the sample by adsorption and allow the fluid sample to progress distally from the point of uptake by, e.g., capillary action. Typically, sample pad 6 is an absorbent member made of fibrous or solid type material. In certain variations, sample pad 6 is a substantially flat porous plastic pad (see, e.g., FIG. 1) such as those known and used in the art for fluid sample collection (e.g., POREX™). In one alternative embodiment, sample pad 6 is a radially symmetrical solid. For example, FIG. 2 shows sample pad 6' as a hemispherical solid with a plug extending from it for insertion into the housing.

Sample pad 6 is configured so that the shape of its base conforms to the interior shape of the base of the run fluid container 14. In some variations, sample pad 6 is color-coded to indicate, e.g., the type of test to be run, or the type(s) of test(s) with which the sample pad is compatible for use. Sample pad 6 can be pre-treated chemically (e.g., with a compatible detergent or surfactant), or with a plasma, to render the sample pad 6, or a part or parts of it, hydrophilic. In some variations, sample pad 6 is configured for use with either oral fluid or blood. Sample pad 6 can also be configured to allow for variation in sample size.

Figures 3A, 3C:
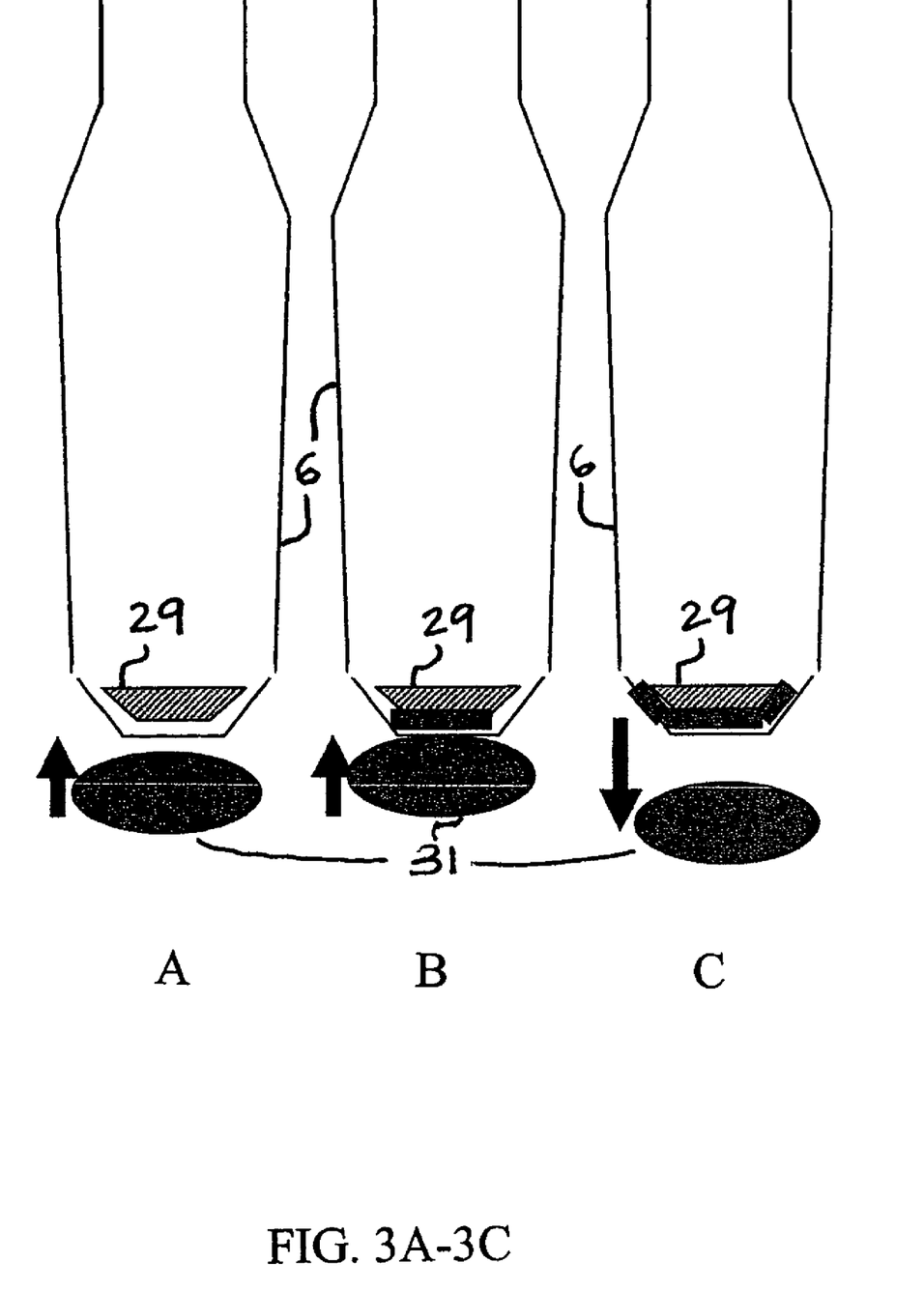

In certain embodiments, sample pad 6 includes one or more markings providing an indication of the appropriate amount of sample to be collected (e.g., fluid to be absorbed) onto the sample pad 6 for the test reaction. For example, in certain embodiments, sample pad 6 has minimum/maximum sample size indicators. (See, e.g., FIG. 2, which shows embodiments of sample 6 (sample pads 6" and 6'") comprising two markings 26 and 28 corresponding to minimum and maximum amounts of fluid appropriate for the test reaction.) FIGS. 3A-3C show another variation in which sample pad 6 includes a die-cut-out 29 that serves to regulate the uptake volume of a sample fluid.

Run fluid container 14 can be any container that will fit over the portion of the sample pad 6 extending from the first end 10 of housing 8. In typical embodiments, run fluid container 14 is a polyethylene or polypropylene container with a snap-cap top (e.g., a 2 mL microfuge tube) and having a relatively shallow-angled "V" shaped or "U" shaped base. The run fluid container 14 may also include a liquid diluent suitable for running the corresponding test reaction. In such variations, the run fluid container will typically include a cover 24, such as, e.g., a peel away foil cover or a snap-cap top. The run fluid container 14 is typically configured to fit in a test tube rack or other suitable device that will maintain the container 14 in a substantially upright position and thereby hold the sample testing device in a substantially upright, inverted position when sample pad 6 is placed into the run fluid container 14. In a preferred embodiment, the housing 8 and run fluid container 14 are configured to form an air-tight seal when the run fluid container 14 is positioned over the sample pad 6. The air-tight seal helps to isolate the sample and device components directly contacting the sample, thereby further protecting the user from potentially hazardous test substances (e.g., infectious body fluids).

In some embodiments, the device of the present invention includes a flexible collar 20 that fits into the first end 10 of housing 8. In certain variations, flexible collar 20 is made of santoprene or other appropriate rubber material. Flexible collar 20 has an opening 22, typically in its center, of appropriate dimensions to hold the base of the test strip, including the region of overlap between the test strip 2 and the sample pad 6. Preferably, flexible collar 20 has a flange (not shown) on one end that extends beyond the edge of the outer diameter of housing 8 to allow a snug fit in the run fluid container 14. In a particularly preferred embodiment, the flexible collar allows for an air-tight seal to be formed with the interior of the run fluid container 14 when the run fluid container 14 is positioned over the sample pad 6. The air-tight seal can be achieved, for example, by a snug fit of the run fluid container 14 against the flange of flexible collar 20. Flexible collar 20 can be appropriately labeled or color-coded to indicate, e.g., the particular type of test to be run. Color-coding of the flexible collar 20 can, for example, correspond to the color of the run fluid container 14. Flexible collar 20 can be configured to accommodate different strip/sample combinations. For example, due to variations of sample size and/or volume of diluent, the width of the strip can vary. The flexible collar 20 can be molded to increase the inner diameter of the opening 22 to accommodate various widths of test strip 2.

The device can further include a cover or "sheath" (not shown in FIG. 1) that is configured to be positioned over sample pad 6 and fit snugly over end 10 (and/or over flexible collar 20), thereby protecting the samples pad 6 until it is ready for use. Such a cover or sheath is shown (32a or 32b) in FIG. 5 with respect to a dual test strip device, described hereinbelow.

Figures 4A, 4D:
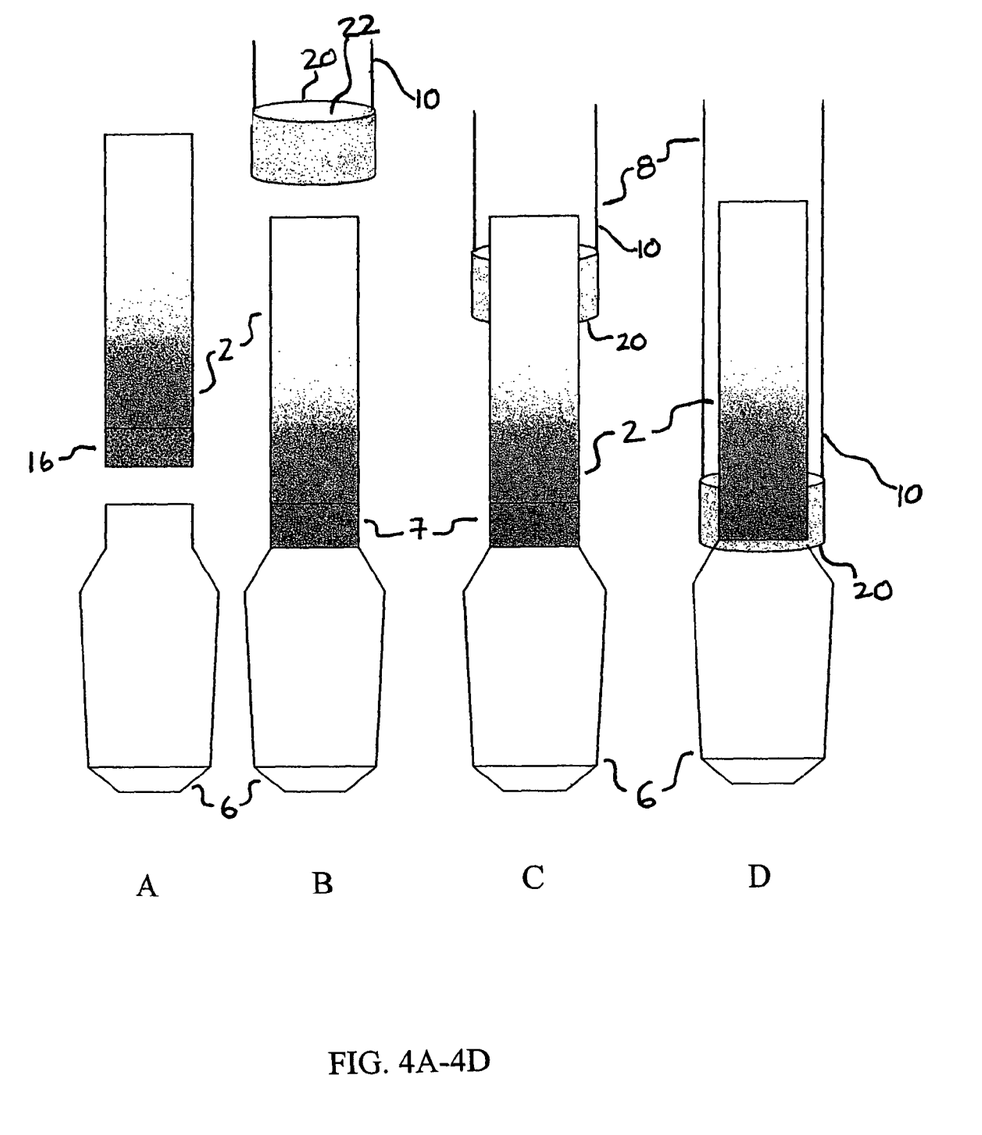

FIGS. 4A-D show one exemplary method of assembling a device of the present invention. FIG. 4A shows the test strip 2 and sample pad 6 prior to coupling. Flexible collar 20 is inserted into first end 10 of housing 8 (FIG. 4B). After coupling of sample pad 6 to the base 16 of test strip 2, forming overlap region 7, test strip 2 is inserted through the opening 22 of flexible collar 20 (FIG. 4C). In certain variations, insertion of the test strip 2 through opening 22 is achieved by gently squeezing the housing/collar subassembly to widen the opening 22, allowing test strip 2 to fit through. The widening of sample pad 6 from the region of coupling to test strip 2 prevents further insertion of the strip/sample pad combination into the housing/collar subassembly (FIG. 4D). Optionally, a sheath may be placed over sample pad 6 to protect the sample pad 6 prior to use (not shown).

In some embodiments, the sample testing device of the present invention includes two sample pad/test strip combinations for collecting two separate samples and running two corresponding test reactions (a "dual test strip" device). Such a device can include two of the sample testing devices as described above coupled in an inverted configuration (with each sample pad 6 at opposite ends) and such that each test strip 2 can be visualized and interpreted through the housing(s). Such a dual test strip device can be achieved, for example, by coupling two housings 8 of two separate devices as described above (e.g., snap-fitted or glued). In other variations, the device comprises two sample pad/test strip combinations assembled into one housing, with the test strips disposed within the housing such that each can be visualized and interpreted.

Figure 5:
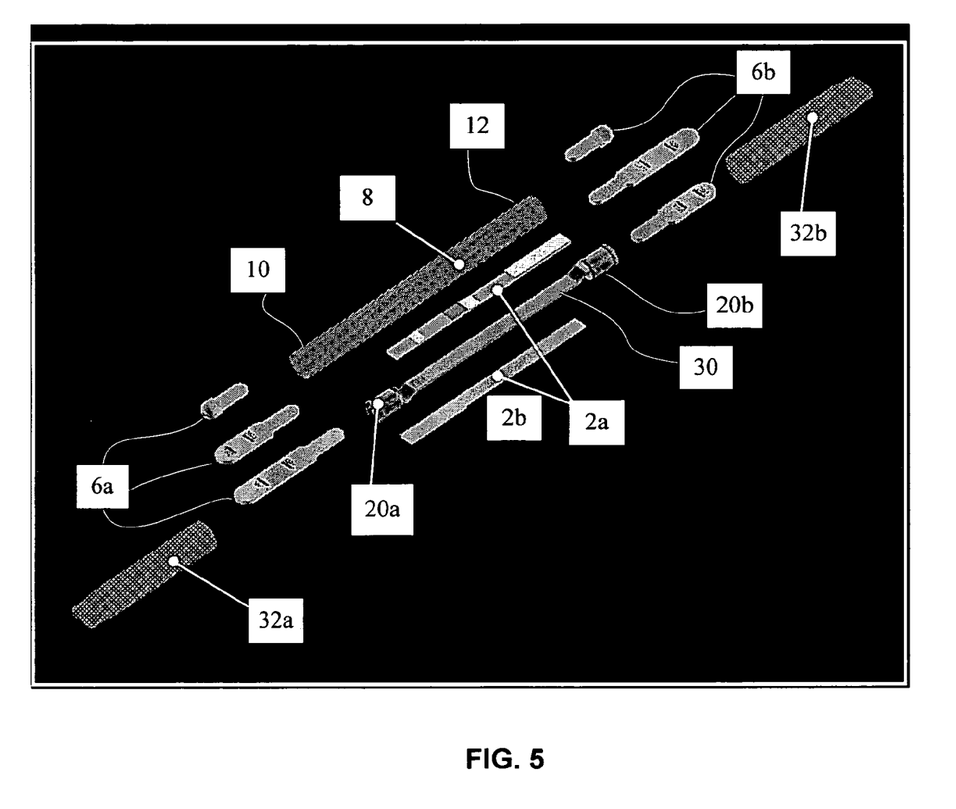
FIG. 5 shows separate components of an embodiment of a dual test strip sample testing device comprising two single sample pad/test strip combinations.
Figure 6:
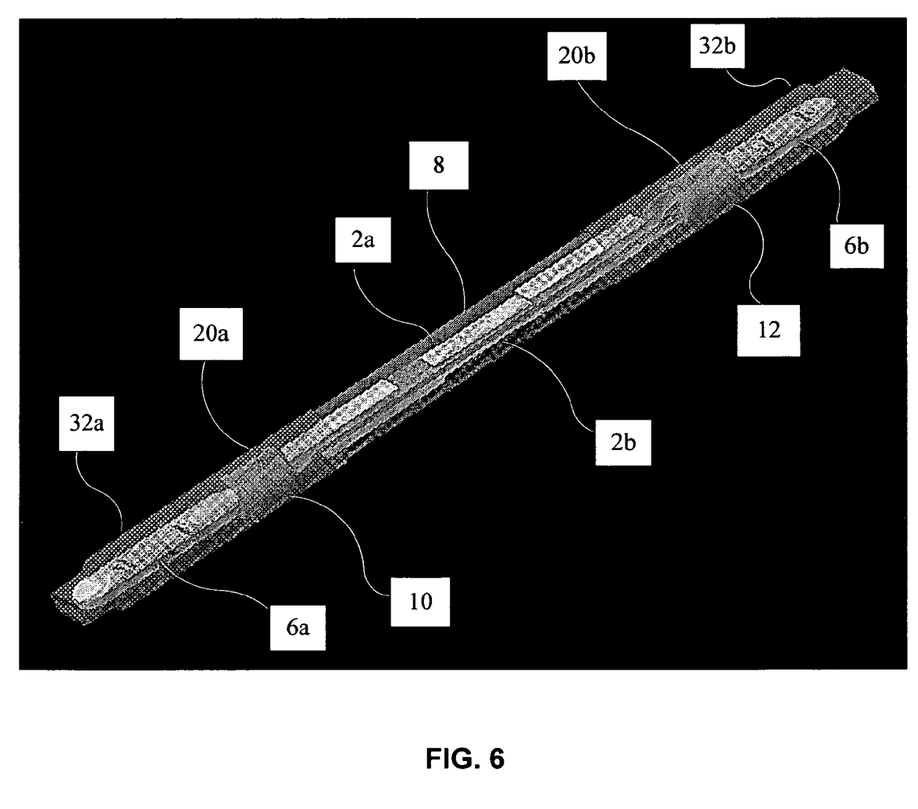
FIG. 6 shows the dual test strip sample testing device of FIG. 5 fully assembled.

FIG. 5 shows the components for one embodiment of a dual test strip device. The device includes housing 8 including ends 10 and 12, two test strips 2a and 2b, two sample pads 6a and 6b, and two flexible collars 20a and 20b. The device can further include a separator element 30 for separating the two sample pad/test strip combinations. In the embodiment shown in FIG. 5, flexible collars 20a and 20b are disposed at opposite ends of separator element 30 such that insertion of test strips 2a and 2b will position the test strips on opposite sides of separator element 30 in an inverted, back-to-back configuration. The back-to-back configuration of test strips 2a and 2b allows each test strip to be visualized within housing 8 by the user, while separator element 30 further prevents cross-contamination. The device can also include covers 32a and 32b (e.g., blow-molded covers) configured to be positioned over sample pads 6a and 6b and fit snugly over corresponding ends 10 and 12 (and/or over flexible collars 20a and 20b), thereby protecting the samples pads 6a and 6b until each is ready for use. FIG. 6 shows the dual test strip device of FIG. 5 in a fully assembled configuration.

The present invention also provides methods for detecting the presence or absence of an analyte in a substance, including biological fluids or other substances, such as for chemical or environmental evaluations, including, for example, dry substances (e.g., anthrax, carbon) or non-biological fluids.

Generally, the method includes collecting the substance with sample pad 6, coupled to test strip 2 enclosed within housing 8; retaining contact of the sample pad 6 with the substance until a sample sufficient for running the test reaction has been collected; allowing the sample to progress through the sample pad 6 and onto the test strip 2; and reading the presence or absence of the analyte from the indicator region on the test strip 2. In certain embodiments, run fluid container 14 (either without diluent or with an appropriate diluent, if required) is placed over the sample pad 6 to form an air-tight seal around end 10 of housing 8 containing the test strip 2. Alternatively, if a diluent is not used, the cover 32 may be placed over the sample pad 6. In some variations, the method further includes determining whether the amount of sample collected is sufficient for, or exceeds a maximum amount for, performing the test reaction.

In some variations of the method, the sample testing device used is provided with cover 32 protecting sample pad 6 from contamination, which is removed to expose sample pad 6 just prior to collection of the sample.

In certain embodiments in which the substance to be tested is a fluid, the fluid sample is collected by contacting the fluid with sample pad 6; retaining contact of the sample pad 6 with the fluid to allow saturation of the sample pad with the fluid, thereby collecting a fluid sample; and allowing the fluid sample to flow through sample pad 6 and onto test strip 2. The fluid sample can be an oral fluid sample (saliva) blood, plasma, serum, spinal fluid, urine, or any other fluid sample appropriate for the test reaction to be run. The fluid sample can be collected, for example, by placing the sample pad 6 inside the mouth (typically for collecting saliva) and passing it over the gums; by contacting a drop of the fluid with the tip of sample pad 6 (e.g., as for a drop of blood); or by inserting sample pad 6 into a container holding the fluid to be tested. In some variations, the sample pad 6 is saturated until a guide is triggered indicating sufficient sample quantity for the test reaction (e.g., a marking 26 on the sample pad indicating a minimum amount of fluid for the test reaction), and sample pad 6 is withdrawn from contact with the fluid prior to a maximum amount of fluid appropriate for the test reaction is collected (which can be indicated, for example, by marking 28 on the sample pad 6 indicating such a maximum). FIGS. 3A-3C show another embodiment in which a die-cut-out 29 in sample pad 6 is used to regulate the uptake of fluid. In this variation, a droplet 31 of fluid is contacted with sample pad 6 so that the sample pad begins to fill with fluid (FIG. 3B) and, when the edge is filled (e.g., to the top of the triangle cut-out 29, the sample pad 6 is withdrawn from contact with the droplet 31 (FIG. 3C).

Should testing on a dry substance be desired, such as for environmental or chemical testing, sample pad 6 would be contacted with the dry substance to collect a dry sample, such as, for example, by swabbing. Use of the sample testing device for testing of dry samples typically requires a diluent that will work with test strip 2. In certain embodiments, the diluent is contained in run fluid container 14. In alternative variations, sample pad 6 may include the diluent (e.g., having an internal pod that is prefilled with the diluent). In those embodiments in which sample pad 6 contains the diluent, cover 32 or empty run fluid container 14 may be placed over sample pad 6 and end 10 of the housing following sample collection. In yet other embodiments, two diluents may be mixed by using a first diluent contained in sample pad 6, which is mixed with a second diluent contained in run fluid container 14 when sample pad 6 is placed into the run fluid container and immersed in the second diluent.

In certain embodiments, following collection of the sample, run fluid container 14 is pressed and secured over the sample collection end of the device, covering sample pad 6 and at least part of end 10 of housing 8 containing test strip 2 (and/or over flexible collar 20, if present). This protects the user and the test from possible contamination, and also helps prevent cross-contamination. In some variations, run fluid container 14 creates an air-tight seal over the end 10 of housing 8 or flexible collar 20, such as by positioning the run fluid container 14 so that there is a sufficiently snug fit of the run fluid container against the flange of flexible collar 20.

With some samples or test reactions (e.g., cardiac markers in whole blood samples), diluent is not used. In this case, the empty run fluid container 14, or cover 32, may be placed over sample pad 6 once the required amount of sample is collected. In certain variations in which the sample or test reaction requires a diluent (e.g., tests for HIV or TB), the sample pad 6 is inserted into a run fluid container 14 containing an appropriate amount of corresponding diluent so that sample pad 6 is immersed in the diluent, typically with the base of sample pad 6 at the base of the run fluid container 14, and the run fluid container 14 is pressed and secured over the end of the device.

Figures 7A, 7C:
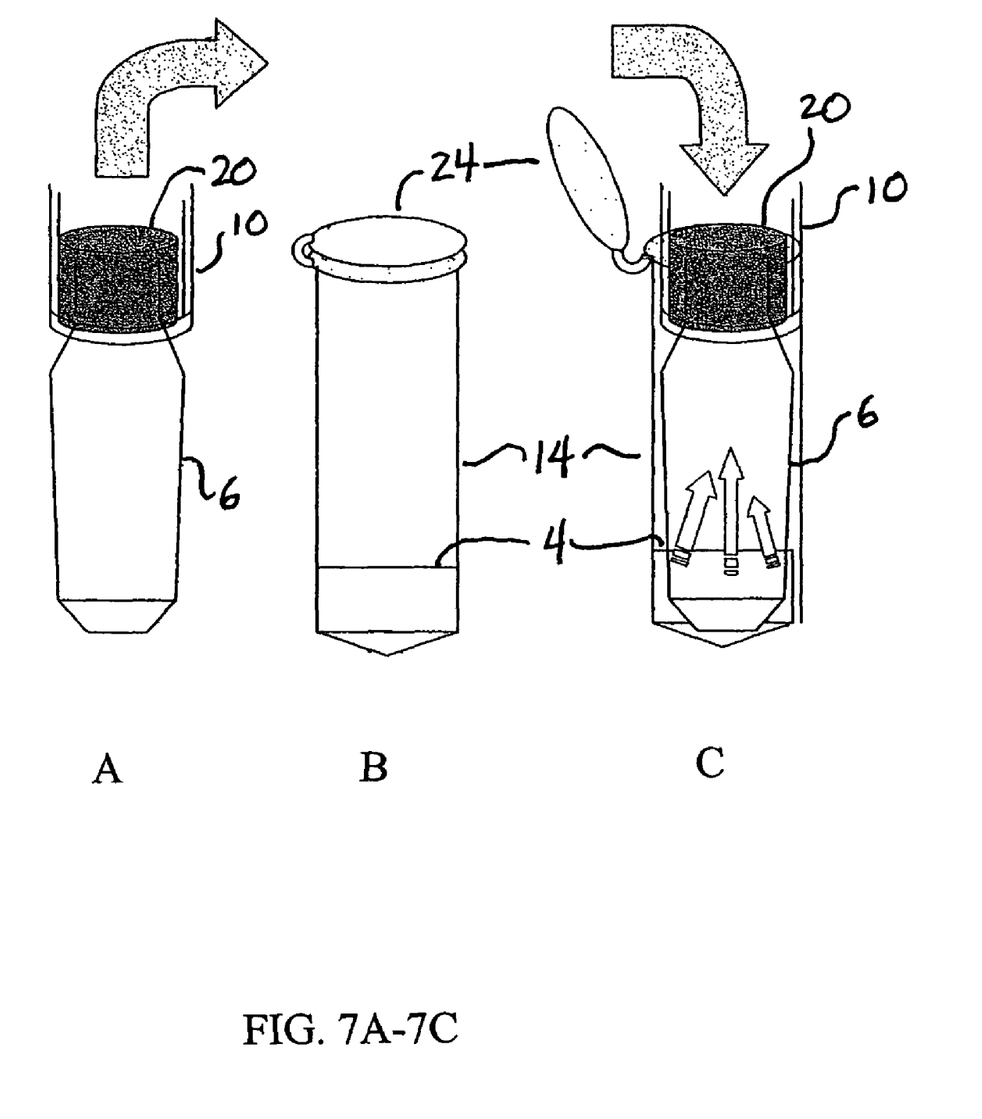

FIGS. 7A-7C further illustrate one embodiment in which sample pad 6 at the end of the sample testing device (FIG. 7A) is used with a run fluid container 14 containing a diluent (FIG. 7B). Sample pad 6 is inserted into the opened run fluid container 14 so that the base of the pad is immersed in diluent, allowing diluent to fill the sample pad 6 and flow onto the test strip (not shown), and so that the flexible collar 20 of the device seals along the inside of the container wall (FIG. 7C). The run fluid container 14, with the sample pad 6 of the testing device inserted, can be inserted into a rack for the duration of the test run (e.g., such as microfuge tube rack in the case of a 2 mL microfuge run fluid container), such as, for example, in an upright position, or can be placed in a substantially flat or elevated position.

The sample is allowed to progress to the indicator region of the test strip 2, where the test automatically initiates and the results are visible on the test strip through the housing 8. If necessary or desired, a timer can be used to indicate to the user an appropriate time for reading the test strip.

In those embodiments in which a dual test strip device is used to collect a sample, if additional or different samples are needed, once one test is being processed on one side, a second test may be initiated on the opposite side. The procedure set forth above is followed with the second end of the device, using the second sample pad 6b to collect the second sample. The second sample pad 6b may also be covered with cover 32b or, alternatively, run fluid container 14b, with or without diluent, as appropriate to the particular sample or test reaction.

In another aspect, the present invention provides a kit for testing a substance for the presence or absence of an analyte, the kit including at least one sample testing device as described herein. In certain embodiments, the kit includes run fluid container 14 containing a suitable diluent for running the test reaction. The run fluid container 14 is typically segregated (e.g., in a different compartment) from the sample collection assembly 11 comprising test strip 2, sample pad 6, housing 8 and optionally flexible collar 20. Typically, sample collection assembly 11 is provided with cover 32 disposed over sample pad 6 and end 10 of housing 8 to protect sample pad 6 from contamination prior to sample collection. The kit can also include instructions for using the device according to one or more of the methods as described herein.

Figure 8:
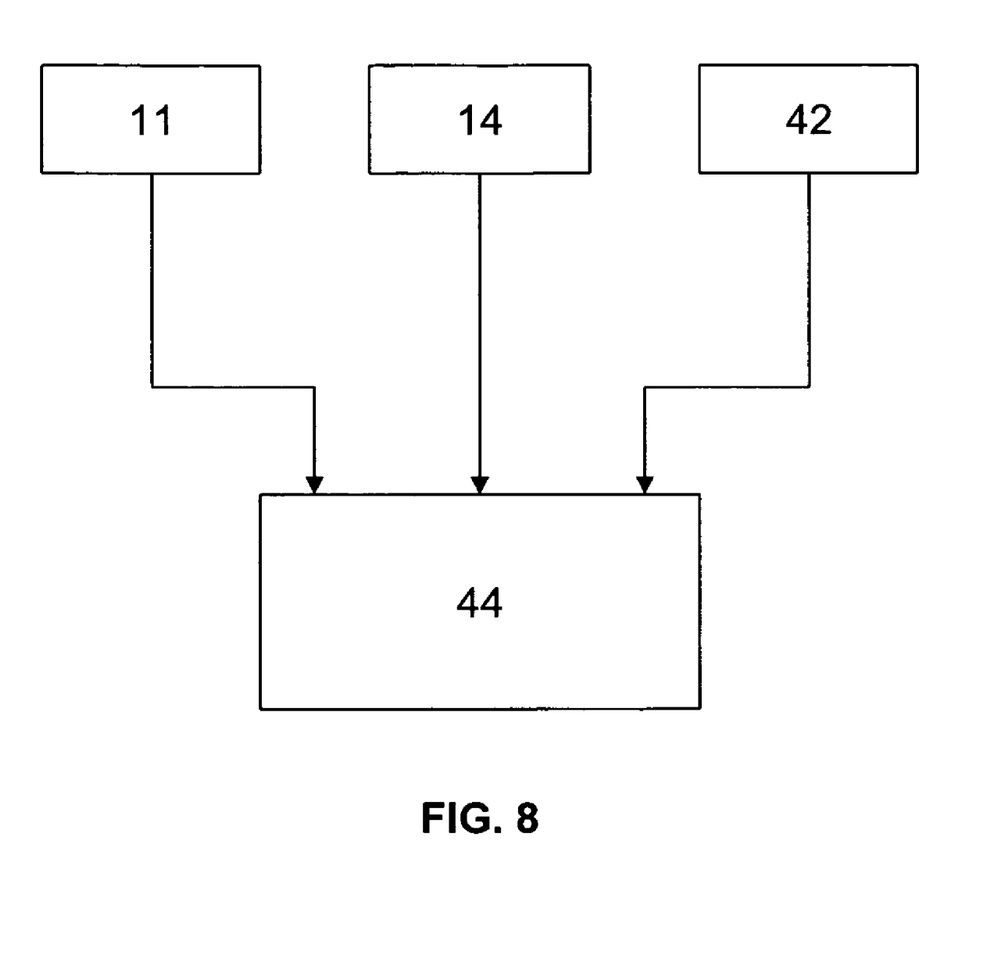
FIG. 8 depicts a kit of the present invention comprising a sample collection assembly, a run fluid container, and instructions for use contained within a package.

FIG. 8 schematically shows an exemplary kit 40 of the present invention. The kit 40 may include sample collection assembly 11, run fluid container 14, instructions for use (IFU) 42, and at least one package 44. Sample collection assembly 11 and run fluid container 14 will generally be as described above, and the instructions for use (IFU) 42 will set forth any of the methods described above. Package 44 may be any conventional device packaging, including, e.g., pouches, trays, boxes, tubes, or the like. IFU 42 will typically be printed on a separate piece of paper, but may also be printed in whole or in part on a portion of the package 44.

What is claimed is:

1. A device for performing a test reaction on a sample to detect an analyte, comprising:
    a sample pad for collecting the sample, the sample pad comprising at least one marking providing a visual indication of the amount of sample collected, wherein the at least one marking is disposed and located on the sample pad so as to provide visual measurement indication, in both the presence or absence of sample, of a minimum or maximum amount of sample to be collected for delivering sample to the test strip for determining a presence or absence of an analyte in the sample;
    a test strip coupled to the sample pad, the test strip comprising an indicator region configured to provide a visual indication of the presence or absence of the analyte in the sample; and
    a housing comprising a first end and a second end, wherein the test strip is disposed within the housing, the housing allowing visualization of the test strip, and wherein at least a portion of the sample pad extends beyond the first end of the housing.

2. The device of claim 1, wherein the device is configured for testing a fluid sample.

3. The device of claim 1, comprising at least two markings providing a visual indication of the amount of sample collected.

4. The device of claim 3, wherein the at least two markings providing a visual indication of the amount of sample collected comprise
    a first marking indicating a minimum amount of sample sufficient for performing the test reaction; and
    a second marking indicating a maximum amount of sample for performing the test reaction.

5. The device of claim 1, further comprising a run fluid container configured to be positioned over the portion of the sample pad that extends beyond the first end of the housing.

6. The device of claim 1, wherein the run fluid container contains a diluent.

7. The device of claim 1, further comprising a flexible collar at the first end of the housing, wherein the flexible collar allows insertion of the sample pad and the test strip into the housing and is configured to maintain coupling of the test strip to the sample pad.

8. The device of claim 7, wherein the flexible collar comprises a color providing a visual indication of the test reaction to be performed.

9. The device of claim 5, wherein at least one of the run fluid container and the test strip comprises a color providing a visual indication of the test reaction to be performed.

10. The device of claim 5, further comprising:
    a second sample pad for collecting a second sample; and
    a second test strip coupled to the second sample pad, the second test strip comprising a second indicator region configured to provide a visual indication of a second test reaction with the second sample;
    wherein the second test strip is disposed within the housing, the housing allowing visualization of the second test strip, and wherein at least a portion of the second sample pad extends beyond the second end of the housing.

11. The device of claim 10, further comprising a second run fluid container configured to be positioned over the portion of the second sample pad that extends beyond the second end of the housing.

12. The device of claim 10, further comprising a fluid-impermeable element that separates the first and second sample pads.

* * * * *